US012691010B2

(12) United States Patent
Hoffmann

(10) Patent No.: US 12,691,010 B2
(45) Date of Patent: Jul. 28, 2026

(54) EARPAD COMPRISING ONE OR MORE RESONATORS

(71) Applicant: Sony Group Corporation, Tokyo (JP)

(72) Inventor: Falk-Martin Hoffmann, Stuttgart (DE)

(73) Assignee: SONY GROUP CORPORATION, Tokyo (JP)

( * ) Notice: Subject to any disclaimer, the term of this patent is extended or adjusted under 35 U.S.C. 154(b) by 86 days.

(21) Appl. No.: 18/280,683

(22) PCT Filed: Mar. 15, 2022

(86) PCT No.: PCT/EP2022/056760
§ 371 (c)(1),
(2) Date: Sep. 7, 2023

(87) PCT Pub. No.: WO2022/200134
PCT Pub. Date: Sep. 29, 2022

(65) Prior Publication Data
US 2024/0139034 A1     May 2, 2024

(30) Foreign Application Priority Data
Mar. 24, 2021     (EP) .................................... 21164659

(51) Int. Cl.
*A61F 11/14*          (2006.01)
*H04R 1/10*           (2006.01)
(52) U.S. Cl.
CPC .......... *A61F 11/145* (2022.01); *H04R 1/1008* (2013.01); *H04R 1/1083* (2013.01)

(58) Field of Classification Search
CPC ...... A61F 11/14; A61F 11/145; H04R 1/1008; H04R 1/1083; G10K 11/04; G10K 11/172
See application file for complete search history.

(56) References Cited

U.S. PATENT DOCUMENTS

| | | | |
|---|---|---|---|
| 4,441,576 A | 4/1984 | Allen | |
| 4,924,502 A | 5/1990 | Allen et al. | |
| 10,469,939 B1 | 11/2019 | Tikander et al. | |
| 10,721,567 B2 | 7/2020 | Kuhr et al. | |
| 2018/0357994 A1 | 12/2018 | Khelif et al. | |
| 2020/0143782 A1* | 5/2020 | Honji .................... | G10K 11/162 |
| 2020/0397618 A1* | 12/2020 | Hua .......................... | H04R 3/02 |
| 2022/0046351 A1 | 2/2022 | Tsuchihashi | |

FOREIGN PATENT DOCUMENTS

| | | |
|---|---|---|
| CN | 101375328 A | 2/2009 |
| CN | 108605180 A | 9/2018 |
| EP | 2 827 608 A1 | 1/2015 |
| | (Continued) | |

OTHER PUBLICATIONS

International Search Report and Written Opinion mailed on Jul. 15, 2022, received for PCT Application PCT/EP2022/056760, filed on Mar. 15, 2022, 13 pages.

(Continued)

*Primary Examiner* — Paul W Huber
(74) *Attorney, Agent, or Firm* — XSENSUS LLP

(57) ABSTRACT

An earpad comprising one or more acoustic resonators coupled to a contact face of the earpad that is configured to interface with a user's head, the acoustic resonators being configured to attenuate leakage of parasitic sound.

20 Claims, 9 Drawing Sheets

(56) References Cited

FOREIGN PATENT DOCUMENTS

| JP | S51-144105 | A | 12/1976 |
|----|-----------|---|---------|
| JP | H04-123598 | A | 4/1992 |
| JP | 2004-500747 | A | 1/2004 |
| JP | 2006-174229 | A | 6/2006 |
| WO | 2019/109389 | A1 | 6/2019 |

OTHER PUBLICATIONS

Michael Talbot-Smith, "Audio Engineer's Reference Book", Focal Press, Second Edition (1999), 2 pages.
Blauert et al.,"Acoustics for Engineers", Troy Lectures, Springer, 2008, 2 pages.
Groby et al., "The use of slow waves to design simple sound absorbing materials", Journal of Applied Physics, vol. 117, No. 124903, Mar. 25, 2015, pp. 124903-1-124903-9.
Groby et al., "Use of slow sound to design perfect and broadband passive sound absorbing materials", The Journal of the Acoustical Society of America, Acoustical Society of America, vol. 139, No. 4, Apr. 6, 2016, pp. 1660-1671.
Jiménez et al., "Quasi-perfect absorption by sub-wavelength acoustic panels in transmission using accumulation of resonances due to slow sound", arXiv:1610.04645v1 [physics.class-ph], Oct. 13, 2016, pp. 1-11.
Casarini et al., "Enhancing the Sound Absorption of Small-Scale 3-D Printed Acoustic Metamaterials Based on Helmholtz Resonators", IEEE Sensors Journal, vol. 18, No. 19, Oct. 1, 2018, pp. 7949-7955.
Casarini et al., "3D printed small-scale acoustic metamaterials based on Helmholtz resonators with tuned overtones", IEEE Sensors, Oct. 29-Nov. 1, 2017, pp. 1-3.
Casarini et al., "Enhancing the Sound Absorption of Small-Scale 3D Printed Acoustic Metamaterials Based on Helmholtz Resonators", IEEEXplore, Available Online at: https://ieeexplore.ieee.org/abstract/document/8234381/, Apr. 17, 2018, pp. 1-8.
Koutserimpas et al., "Active Acoustic Resonators with Reconfigurable Resonance Frequency, Absorption, and Bandwidth", Physical Review Applied, vol. 12, No. 054064, 2019, pp. 054064-1-054064-10.

* cited by examiner

EARPAD COMPRISING ONE OR MORE RESONATORS

CROSS-REFERENCE TO RELATED APPLICATIONS

The present application is based on PCT filing PCT/EP2022/056760, filed Mar. 15, 2022, which claims priority from European Patent Application No. 21164659.1, filed Mar. 24, 2021, the entire contents of each are incorporated herein by reference.

TECHNICAL FIELD

The present disclosure generally pertains to the field of sound attenuation, in particular to an earpad with one or more resonators for attenuation of external sound sources.

TECHNICAL BACKGROUND

The use of headphones for listening to music, podcasts or the like is becoming increasingly widespread in the wake of the increasing use of mobile music players such as smartphones, tablets or the like. However, when listening with headphones, external sound sources can interfere with the listening experience. Also, hearing protection is an important issue with many application areas, for example in industries such as in steel mills. To prevent damages to the hearing, attenuation of external sound sources is an important issue. For example, in state-of-the art headphones and circumaural hearing protection, sound attenuation can be achieved by the earpads of the headphones or the hearing protection, respectively. Also, sound attenuation can be achieved by the hard-shell housings that are holding the earpads, which can be made from traditionally absorbing or reflecting materials.

However, in general, in order to attenuate an external sound source, it is required that the earpad makes a perfect seal around the ear. If this is not the case, the external sound may reach the cavity beyond the earpad, thus compromising the performance of the headphones/hearing protection and disturbing a listening experience or putting the hearing at risk.

Therefore, it is desirable to further improve the attenuation of external sound sources in headphones and/or hearing protections.

SUMMARY

The disclosure provides an earpad comprising one or more acoustic resonators coupled to a contact face of the earpad that is configured to interface with a user's head, wherein the acoustic resonators are configured to attenuate parasitic leakage of sound.

Further aspects are set forth in the dependent claims, the following description and the drawings.

BRIEF DESCRIPTION OF THE DRAWINGS

Embodiments are explained by way of example with respect to the accompanying drawings, in which.

DETAILED DESCRIPTION OF EMBODIMENTS

Figure 1:
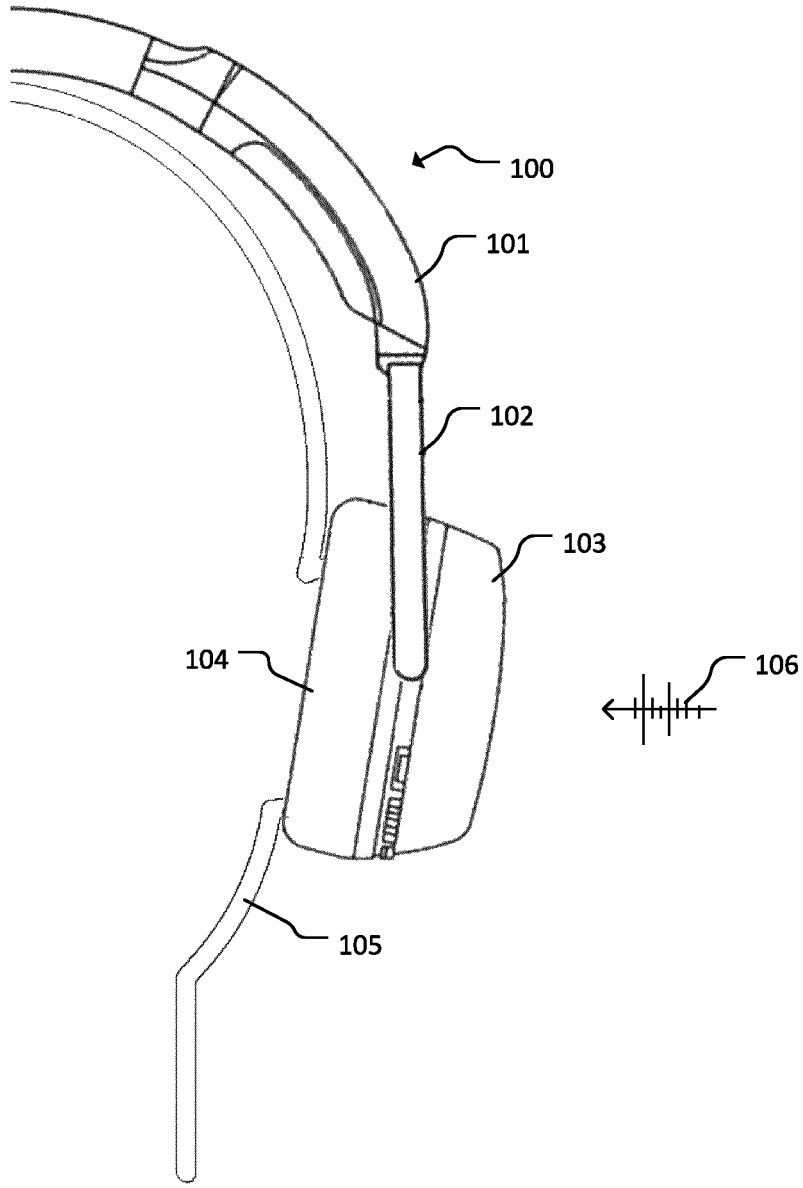
FIG. 1 shows a user wearing a circumaural headphone.

Before a detailed description of the embodiments under reference of FIG. 1, general explanations are made.

The embodiments described below in more detail disclose an earpad comprising one or more acoustic resonators coupled to a contact face of the earpad that is configured to interface with a user's head, wherein the acoustic resonators are configured to attenuate leakage of parasitic sound.

The resonators are configured to attenuate sound from an external source on a parasitic leak channel, to reduce transmission to the inside of the headphone/earphone.

The earpad may be included in an on-ear headphone or a circumaural headphone. The earpad may also be included in an on-ear or circumaural (industrial) hearing protection. A circumaural earpad may fully enclose an ear when a wearer is wearing it properly.

According to some embodiment the resonators may be Helmholtz resonators, or Quarter Wavelength Resonators or, membrane resonators or active acoustic resonators or the like.

Active acoustic resonators may be also described in more detail in the scientific article "Active Acoustic Resonators with Reconfigurable Resonance Frequency, Absorption, and Bandwidth" by Theodoros T. Koutserimpas, Etienne Rivet, Hervé Lissek, and Romain Fleury, published in Phys. Rev. Applied 12, 054064—Published 27 Nov. 2019.

Helmholtz Resonator may comprise a mass channel (also called mass) and a compliance cavity.

A further benefit of the earpad comprising the resonators compared to an active noise cancellation system may be that there may be no technical limitations on the effective frequency band and that no electrical energy and wiring is needed. Therefore, acoustic systems using the earpad comprising the resonators may be highly robust to improper usage (i.e. improper fit) or other user-controlled factors that can create parasitic acoustic leakage, e.g. the wearing of glasses, earrings, hair, hats and other wearables.

The frequency range where this novel absorber becomes active can be optimised to work in conjunction with other means of noise control, i.e. active noise control systems or porous absorbers.

According to some embodiment the acoustic resonators may be configured to attenuate the propagation of a parasitic sound based on a specific acoustic impedance of the resonators and surface porosity due to the resonators on the parasitic channel.

The specific acoustic impedance of the resonators and the surface porosity due to the resonators may have different values for different resonators and frequencies and may be freely designed.

Attenuation, or acoustic attenuation, may be a measure of the energy loss of sound propagation of a sound wave in media. The acoustic attenuation may occur due to absorption in media.

A parasitic sound may originate from an external sound source whose radiated wave are impinging onto the earpad. The parasitic sound may be a sound that should not reach the inner part of the earpad (for example the headphone cavity) but does so due to the occurrence of a parasitic leak path connecting the exterior and the interior of the headphone/earphone. This may be sound like road noise or the like.

According to some embodiment, interfaces to the acoustic resonators may be located at the contact face of the earpad.

The sound waves of the parasitic sound may need to enter the resonators in order to be attenuated. The interfaces to the acoustic resonators may be therefore be located at the contact face of the earpad.

According to some embodiment the earpad may comprise a core material and a cover material, the cover material acting as the contact face of the earpad, wherein the cover material is perforated at the areas of the interfaces of the resonators.

The one or more resonators may be made of the core material.

The core material may be acoustically rigid materials such as silicone, aluminum, styrofoam or the like.

The cover material may be mechanically soft and flexible materials like leather or faux leather, PU foam, fabric, polymers or the like.

In another embodiment the core material may also be encapsulated in more than just one cover material. For instance, the core material may first be wrapped in a soft and flexible foam (e.g. PU foam or the like), which is then itself covered by a smoother material (e.g. leather, faux, leather, fabric or the like).

According to some embodiment the acoustic resonators are configured to attenuate the propagation of parasitic sound within a predefined target frequency band (F).

The acoustic attenuation of the parasitic sound may occur or not occur depending on the frequency of the parasitic sound. The target frequency band may define all the frequencies of a parasitic sound that may be attenuated.

According to some embodiments the predefined target frequency band may be defined by the specific acoustic impedance of the resonators, the surface porosity due to the resonators and a resonance frequency of the resonators.

Still further, a height of a leak channel between resonators and the head of wearer may influence the effective attenuation band as well.

The resonance frequency of the resonators may have different values for different resonators and may be freely designed.

According to some embodiments the lower limit of the frequency band is based on the resonance frequency of the resonators.

According to some embodiments the surface porosity due to the resonators may be 0.4.

The contact face of the resonators may be a plane, that is periodic, i.e. it has a lattice. The lattice constant in both x and y-direction may be the same, namely b. Then each segment in the lattice may have an area $B=b^2$, where $[B]=m^2$. Further, a size of an area where the resonator interfaces its associated lattice segment of the contact face may be denoted as A, where $[A]=m^2$. Then the surface porosity due to the resonators might be defined as $$\Phi_R = \frac{A}{B},$$

where $[\Phi_R]=1$. According to some embodiments the specific acoustic impedance of the resonators may be frequency dependent. A graph that shows the frequency dependent specific acoustic impedance of the resonators may be shown in FIGS. 7a and 7b.

According to some embodiments the resonators may be Helmholtz resonators, each Helmholtz resonator comprising a mass channel and a compliance cavity.

According to some embodiments the compliance cavities of the Helmholtz Resonators may be combined into a joint compliance cavity which may be connected to each of the mass channels of the Helmholtz Resonators.

According to some embodiments the earpad may comprise a plurality of sections, each of the sections comprising one joint compliance cavity and a plurality of mass channels connected to the one joint compliance cavity.

According to some embodiment the plurality of sections may be separated from each other. The separation of the sections may be carried out by planting a specific material, for example a soundproof material. The separation sections may also be carried out by leaving some space between two sections.

Embodiments are now described by reference to the drawings.

FIG. 1 shows a user wearing a circumaural headphone. The headphone 100 comprises a headband 101 and a left connecting joint (not shown) and a right connecting joint 102 which respectively connect the headband to a left hard-shell housing (not shown) and a right hard-shell housing 103 of the headphone 100. The headphone 100 further comprises a left earpad (not shown) and a right earpad 104, wherein the left and the right hard-shell housing is holding the earpad. The earpad 104 of the circumaural headphone 100 (also called over-ear headphone) rests on the head 105 and is configured to completely enclose the ear. The earpad 104 is made of a common porous absorbing material, like for example a closed-cell polyurethane foam wrapped in (faux) leather or a light rubber (in the case of earmuffs) for a structure for an earpad (where the foam would make for the main bulk of it).

The wearer of the headphones may listen to music while being exposed to sound 106 from external sources. The external sound 106 reaches the headphone cavity and thereby the ear of the wearer. Thereby it can compromise the music listening experience or—if the external sound is very loud—it may damage the hearing of the wearer.

In current headphone technology the acoustic energy of the external sound 106 may be absorbed/attenuated and/or reflected by the hard-shell housing 103 and the earpad 104 before it reaches the headphone cavity. The solid hard-shell housing 103 which is holding the earpad 104 typically has a higher reflection capability than the earpad 104 due to the large acoustic impedance mismatch between the solid hard-shell housing 103 and the air. As described in the scientific textbooks "Audio Engineer's Reference Book", by Talbot-Smith, Focal Press (1999), p. 264, and "Acoustics for Engineers", by Blauert, Xiang, Springer (2008), p. 209 the attenuation (or insertion loss) achieved by passive headphones (i.e. by the solid hard-shell housing 103 and the earpad) can reach up to 40 dB. Accordingly, it is to be expected that the earpad 104 is the weakest point with respect to acoustic insulation of the headphone cavity from the outside world.

Figure 3:
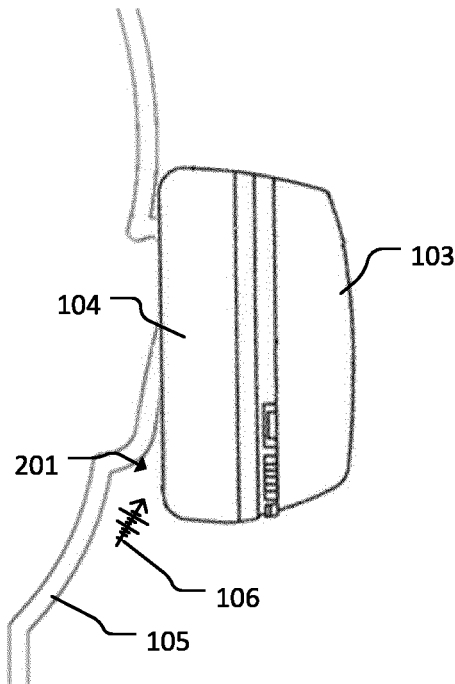
FIG. 3 shows an earpad of a headphone, the earpad having an imperfect (leaky) connection to the head.

A problem that may arise is that the high values of attenuation (insulation) are only achieved when the contact between the earpad 104 and the head 105 is ideal, i.e. without parasitic leaks (see FIG. 3). If a leak exists between the earpad 104 and the head 105, the waves (of the external sound source 106) may have a propagation path past the absorbing earpad 104 and can therefore enter the headphone cavity, and hence the music listening experience or the hearing protection may again be compromised.

Figure 2:
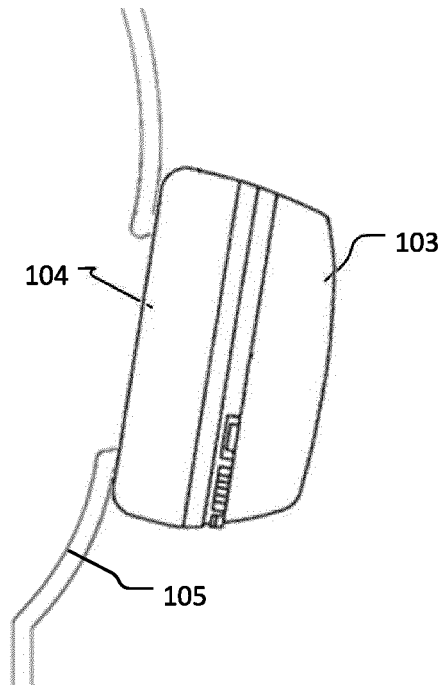
FIG. 2 shows an earpad of a headphone, the earpad having a leakless connection to the head and the hard-shell housing.

FIG. 2 shows an earpad of a headphone, the earpad having a leakless connection to the head. The earpad 104 completely encloses the ear and it has a complete connection to the head 105 of the wearer of the headphone 100. Therefore, sound 106 from an external sound source may not reach the headphone cavity (or be highly attenuated at least).

FIG. 3 shows an earpad of a headphone, the earpad having an imperfect (leaky) connection to the head. Between the earpad 104 and the head 105 of a wearer of headphone 100 is a leak 201. Sound 106 from an external sound source may enter the cavity of the headphone and thereby compromise the music listening experience or the hearing protection.

Figure 4:
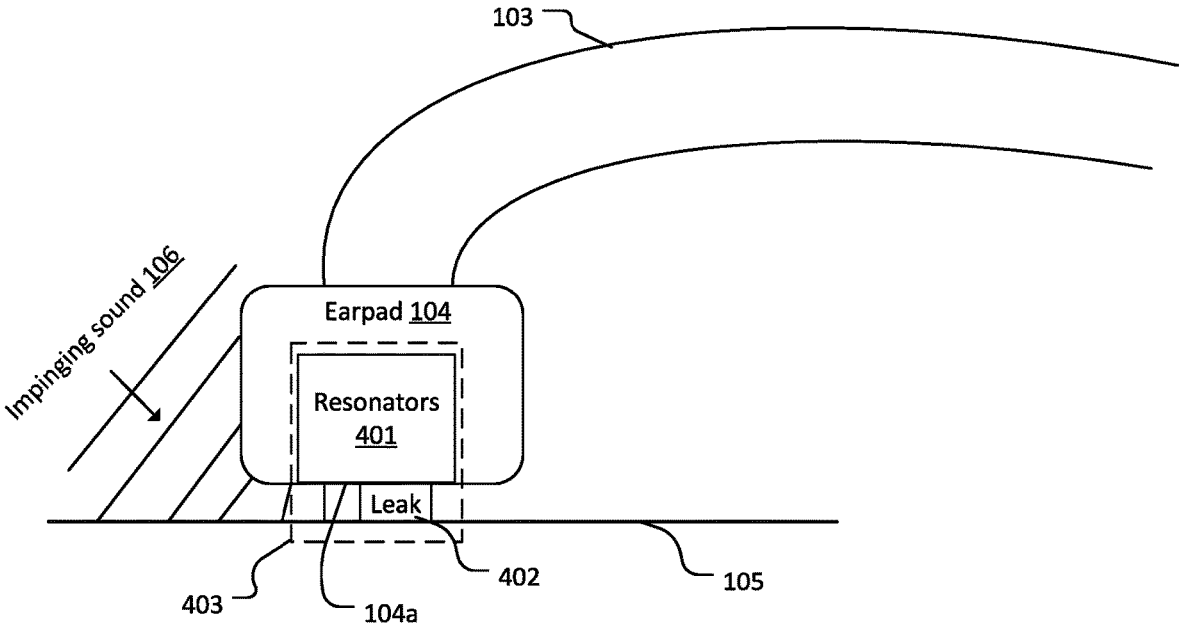
FIG. 4 shows a longitudinal cross-section through an earpad with one or more resonators which are configured to attenuate external sound when there is a parasitic leak channel.

Using Resonators to Attenuate External Sound Impinging on a Parasitic Leak Channel FIG. 4 shows a cross-section through an earpad with one or more resonators which are configured to attenuate external sound. A hard-shell housing 103 of a headphone is holding an earpad 104. Due to an imperfect fitting of earpad 104, a parasitic leak channel 402 (i.e. an acoustic channel) is formed between the earpad 104 and the head 105. The earpad 104 comprises one or more acoustic resonators 401. These acoustic resonators 401 may for example be Helmholtz Resonators (HRs), Quarter Wavelength Resonators (QWRs), membranes, or active acoustic resonators (as for example described in the scientific article "Active Acoustic Resonators with Reconfigurable Resonance Frequency, Absorption, and Bandwidth" by Theodoros T. Koutserimpas, Etienne Rivet, Hervé Lissek, and Romain Fleury, published in Phys. Rev. Applied 12, 054064—Published 27 November 2019) or the like. The resonators 401 are connected to a contact face 104a of the earpad 104. That means, an interface to the acoustic resonators 401 may be located directly at the contact face 104a of the earpad. For example, the material of the contact face 104a of the earpad (for example leather or faux leather) may me perforated at the areas of the interfaces of the resonators 401 (see also FIG. 9 and corresponding description). Thereby, external sound waves impinging on leak channel 402 may directly enter the resonators 401 through their interfaces. In the case of HRs and QWRs the interfaces of the resonators may be realized by openings of the resonators that means the sound waves may "enter" the resonator at the opening. In the case of a membrane resonator or an active acoustic absorber, the sound waves may interact with the interfaces of the resonator instead of actually "entering" it.

The acoustic resonators 401, which are part of the earpad construction, and the parasitic leak channel 402 to which the resonators couple, form together a highly absorbing acoustic meta material 403 (AMM). The AMM 403 created by the parasitic channel 402 and resonators 401 create a very high absorption and an extremely low phase velocity for the acoustic waves of the impinging external sound 106. The technical background concerning this effect of an acoustic meta material (AMM) is also described in the scientific paper "The use of slow waves to design simple sound absorbing materials", by Groby et al, J. Appl. Phys. 117, 124903 (2015) and the scientific paper "Quasiperfect absorption by subwavelength acoustic panels in transmission using accumulation of resonances due to slow sound", by Jimenez et al, Physical Review B 95, 013205 (2017).

If the fit of the earpad is imperfect, according to these principles described above, the external sound 106 which is impinging on the leak 402 is attenuated. If the fit of the earpad is perfect, the resonators effectively lie dormant inside the earpad 104.

Figure 5:
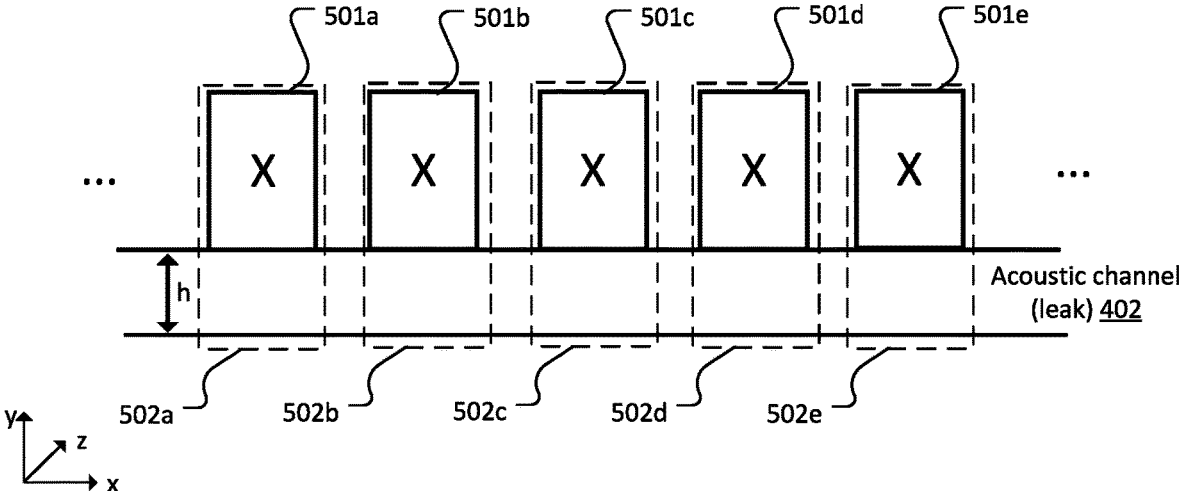
FIG. 5 shows an internal structure of the acoustic metamaterial of FIG. 4.

FIG. 5 shows a schematic representation of the acoustic meta material (AMM) embedded within the earpad of FIG. 4. In this schematic and simplified example, the AMM 403 consists of a single leak channel 402 which has a height h and it further consists of several resonators (resonant elements) 501a, . . . , 501e. Each resonant element 501a, . . . , 501e together with a section of the leak channel 402 to which the resonant element couples, forms a so called "meta-atom". The AMM 403 is composed of a periodic repetition (i.e. the periodicity may occur in both x- and z-direction) 502a, . . . , 502e of meta-atoms, as it is common in metamaterials.

In the example provided here, the meta atoms are preferably distributed as periodically as possible. Naturally, a perfect periodicity may not be always be possible to maintain. However, as long as the resonant elements (for example the mass channels of the Helmholtz resonators in FIG. 8) are significantly smaller than the wavelength, small deviations from periodicity are not a problem to the attenuation effect provided by the resonators.

The total number of meta-atoms (respectively resonators) may depend on the overall dimensions of the earpad and the periodicity of the resonators on the contact face, i.e. the inverse of the area associated with one meta-atom, assuming that meta-atoms leave no gaps between each other.

For AMM, it is common to choose the meta-atom size equal to or smaller than one sixth of the wavelength in air.

Model of Sound Attenuation in AMMs with Acoustic Resonators

The amount of attenuation and the frequency band where the attenuation effected by the resonators is occurring can be determined and designed based on a mathematical model of the acoustic meta material (AMM) generated by the parasitic leak channel and the resonators. This model is based on the resonance frequency of the resonators $f_R$, the specific acoustic impedance $Z_R$ of the resonators, and the surface porosity due to the resonators, $\Phi_R$.

The AMM may be invariant along a third coordinate axis (i.e. axis into the image plane in FIG. 5), so that the model may be simplified to two dimensions. The pressure variation of the propagation of a plane-wave along the x-axis is described by $$p(x) = Ae^{\gamma x}, \tag{1}$$

where A and $\gamma$ are the amplitude and complex propagation constant of sound, respectively. The propagation constant can be divided into a propagation and an attenuation part as follows $$\gamma = \alpha + ik, k = \frac{\omega}{c}, \tag{2}$$

where $\alpha$ and k represent the exponential damping factor and acoustic (angular) wave number respectively, c is the phase velocity, and $\omega$ is the angular frequency of the sound wave.

Using equation (2), equation (1) can be rewritten as $$p(x) = Ae^{\alpha x}e^{ikx}, \tag{3}$$

where a negative value of $\alpha$ corresponds to exponential decay along the channel.

So far, it has been assumed that all higher order (i.e. greater than the 0-th order) wave components along the y-axis are evanescent and therefore do not propagate. However, is shown in the following that the presence of the resonators on one of the boundaries can actually change that.

The following model description is based on the fundamental teachings given by Groby et al in the two scientific papers cited above.

The pressure in the (x,y) plane along the leak channel can be approximated through a pseudo-modal expansion $$p(x, y) = \sum_{n \in \mathbb{N}} A_n \, e^{ik_{x,n}x} \cos(k_{y,n}y), \tag{4}$$

where the index n describes the modes of the expansion, $A_n$ are the coefficients of the pseudo-modal expansion $k_{x,n}$ and $k_{y,n}$ and are the x and y part of the complex wavenumber corresponding to the n-th mode, which are linked together by the absolute value of the angular wave number k as follows $$k_{x,n} = \sqrt{k^2 - k_{y,n}^2}, \tag{5}$$

Further, $k_{y,n}$ must satisfy the dispersion relation $$k_{y,n}\tan(k_{y,n}h) = -\frac{i\omega\rho_{ch}}{Z_R}, \tag{6}$$

where $Z_R$ is the specific acoustic impedance of the resonators that is seen when looking at the boundary that connects the resonators to the leak channel. $\rho_{ch}$ denotes the acoustic density on the leak channel, and h denotes the height of the leak channel.

From a low-frequency approximation, the solution of Equation (6) for n=0 can be found as $$k_{y,0} = \frac{1}{h}\sqrt{-\frac{i\omega\rho_{ch}h}{Z_R}}. \tag{7}$$

The specific acoustic impedance, $Z_R$, is related to the acoustic impedance of the resonator, $$Z_R^{Ac},$$

through the expression $$Z_R = \frac{Z_R^{Ac}S_m}{\Phi_R}, \; [Z_R] = \frac{Ns}{m^3} \tag{8}$$

where $S_m$ denotes the cross-sectional area of the acoustic mass channel in the case of Helmholtz resonators (for other types of resonators a cross-sectional area of the interface between the resonator and the channel may be used). The surface porosity $\Phi_R$ represents the ratio of the area of the resonator coupling to the channel, i.e. $S_m$, and the area associated with one meta-atom.

With equations (5) and (7) the wave number component in direction of the channel (i.e the x-axis) can be identified as $$k_{x,0} = \frac{\omega}{c_x} = \sqrt{k^2 - k_{y,0}^2}, \tag{9}$$

where $c_x$ is the x-component of the phase velocity. Taking equations (7), (9) and $$k = \frac{\omega}{c}$$

into account, the imaginary part of the wave number $k_{x,0}$ can then be stated as follows $$\mathrm{Im}(k_{x,0}) = \mathrm{Im}\left(\sqrt{\left(\frac{\omega}{c}\right)^2 - \left(\frac{1}{h}\sqrt{-\frac{i\omega\rho_{ch}h}{Z_R}}\right)^2}\right), \tag{10}$$

In the case that real part of wave number $k_{y,0}$ is greater than k, that is if the condition $$\mathrm{Re}(k_{y,0}) > k = \frac{\omega}{c_{ch}}, \tag{11}$$

holds, it follows from equation (9) that the imaginary part of the wave number $k_{x,0}$ as stated in equation (10) becomes very strong. Following the considerations in equations (2) and (3), the absorption on the channel in x-direction can then become very high.

That means, the absorption of the resonators in the leak channel in x-direction $\mathrm{Im}(k_{x,0})$ can be influenced by choosing the specific acoustic impedance of the resonators $Z_R$ and the surface porosity $\Phi_R$ under the assumption of a given channel leak height h.

Still further, the frequency band $F=[f_{low}, f_{up}]$, ranging from a lower frequency boundary $f_{low}$ to the upper boundary $f_{high}$, in which absorption occurs depends on the resonator characteristics.

The lower boundary $f_{low}$ of the frequency band $F=[f_{low}, f_{up}]$ is approximately the resonance frequency of the resonators $f_R$, that is $$f_{low} = f_R. \tag{12}$$

This is because at resonance it holds that $|Z_R| \to 0$ and then it follows from Eq. (7), that $k_{y,0}$, becomes very large.

The upper boundary of the frequency band $f_{up}$ (and respectively the upper angular frequency $\omega_{up}$) can be obtained by solving equation (6) and the real part of the solution fulfilling the following constraint $$\mathrm{Re}(k_{y,0}) \approx k = \frac{\omega_{up}}{c}. \tag{13}$$

This yields $$\mathrm{Re}(k_{y,0}) = \mathrm{Re}\!\left(\frac{1}{h}\sqrt{-\frac{i\omega\rho_{ch}h}{Z_R}\Phi}\right) \overset{!}{=} k = \frac{\omega_{up}}{c}. \tag{14}$$

Solving equation (14) numerically for $\omega_{up}$ yields the upper boundary of the frequency band $f_{up}$. That means, the frequency band $F=[f_{low}, f_{up}]$ in which attenuation (absorption) in the leak channel in x-direction of an impinging sound wave with frequency $\omega$ occurs is determined by the resonance frequency of the resonators $f_R$, the impedance of the resonators $Z_R$ and the surface porosity $\Phi_R$ under the assumption of a given channel leak height h.

Figure 6:
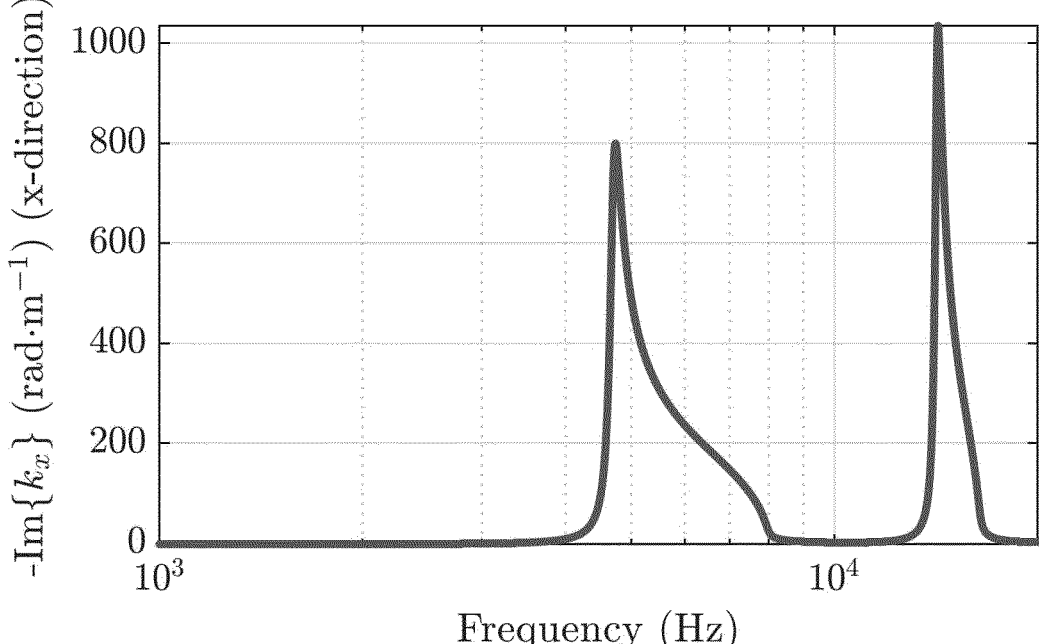
FIG. 6 shows a graph of the frequency-dependent absorption constant in x-direction of a leak channel unilaterally loaded with resonators.

FIG. 6 shows a graph of the frequency-dependent absorption constant $-\mathrm{Im}(k_{x,0})$ in x-direction of a leak channel unilaterally loaded with resonators. The x-axis of the graph shows the frequency in Hz in a logarithmic representation. The y-axis of the graph shows the absorption constant $-\mathrm{Im}(k_{x,0})$ in x-direction of the leak channel unilaterally loaded with resonators in rad/m.

Figure 7A:
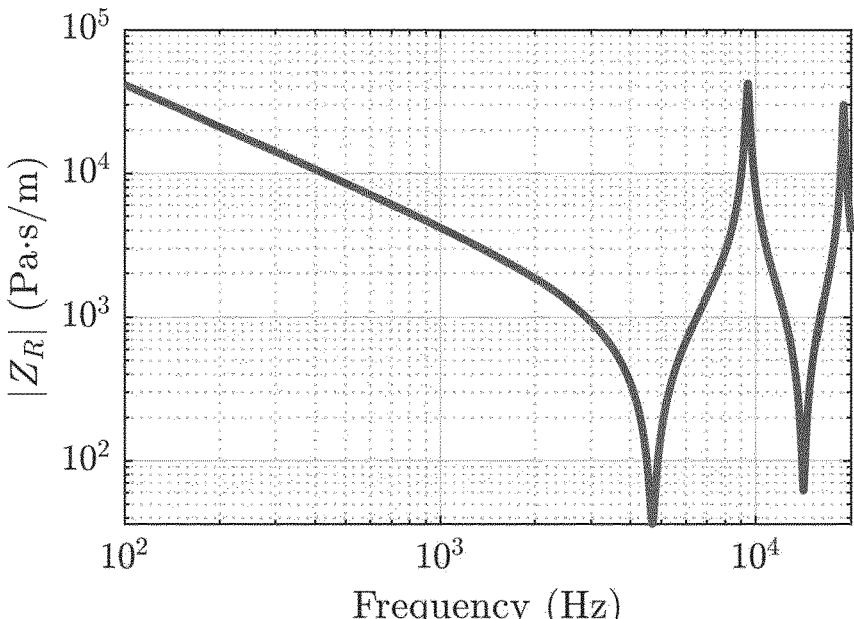
FIG. 7a shows a graph of the frequency-dependent magnitude of the specific acoustic impedance of a resonator.
Figure 7B:
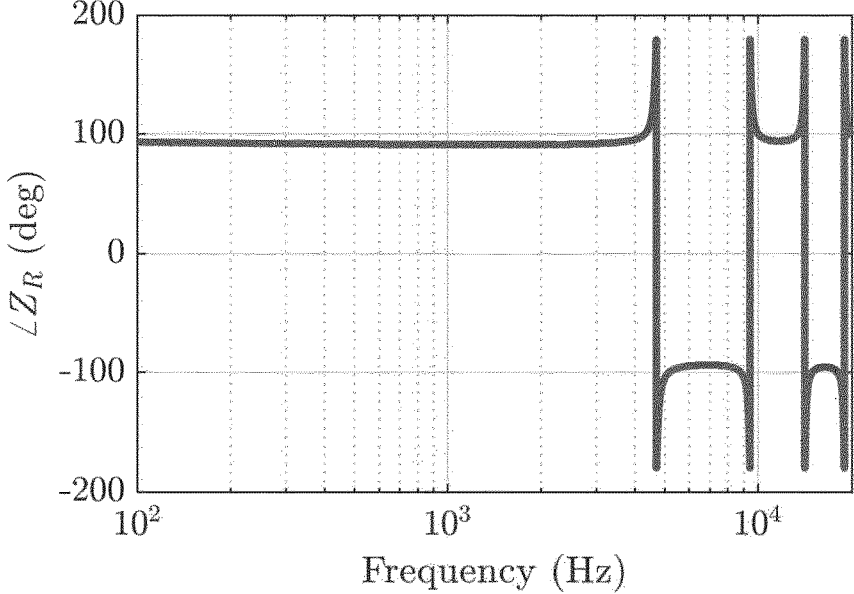
FIG. 7b shows a graph of the frequency-dependent phase of the specific acoustic impedance of a resonator.

FIG. 7a shows a graph of the frequency-dependent magnitude of the specific acoustic impedance of a resonator $|Z_R|$. The x-axis of the graph shows the frequency in Hz in a logarithmic representation. The y-axis of the graph shows the magnitude of the specific acoustic impedance of the resonator $|Z_R|$ in Pa s/m FIG. 7b shows a graph of the frequency-dependent phase of the specific acoustic impedance of a resonator $\angle Z_R$. The x-axis of the graph shows the frequency in Hz in a logarithmic representation. The y-axis of the graph shows the magnitude of the specific acoustic impedance of the resonator $\angle Z_R$ in deg.

Designing the Resonators

According to the considerations made above, according to an embodiment, a plurality of quarter wavelength resonators (QWR) may be used in an earpad of an on-ear or circumaural headphone or in a hearing protection in order to attenuate an impinging external sound source.

The resonators may for example be implemented in a block made of silicone which has a width of 2 cm (x-axis), a height of 2 cm (y-axis) and a depth 2 cm (z-axis). In an equidistant grid structure 32 holes with a diameter of 3 mm are drilled into the silicone block orthogonally to the x-z-plane, wherein each drilled hole is 18 mm deep. Each hole constitutes a QWR.

It is assumed here that an exemplifying parasitic leak channel formed between the head of the user and the earpad has a height of h=1 mm.

Applying the considerations made with regard to the mathematical model of the acoustic metamaterial presented above allows the following conclusions:

This yields a resonance frequency of the resonators of $f_R \approx 4764$ Hz and a surface porosity of $\Phi_R=0.2827$. The specific acoustic impedance of the resonators of $Z_R$ may be as shown in FIGS. 7a and 7b.

It can then be determined the frequency band $F=[f_{low}, f_{up}]$ and the frequency-dependent absorption constant of the resonators in the leak channel in x-direction $\mathrm{Im}(k_{x,0})$ by using equations (9), (11) and (14). This yields a frequency band of F and a frequency-dependent absorption constant of the resonators in the leak channel in x-direction of $\mathrm{Im}(k_{x,0})$ which is for example shown in the graph of FIG. 6.

That is these resonators may be used in an on-ear or circumaural headphone or in a hearing protection in order to attenuate an impinging external sound within the frequency band $F=[f_{low}, f_{up}]=[4764\ \text{Hz}, 8050\ \text{Hz}]$.

In the embodiment described above, the resonators are implemented in a block of silicone. In other embodiments, other materials may be used for the QWRs, for example aluminium or the like.

In yet different embodiments other surface porosities or other dimensions of the resonators may be used.

In the embodiment described here, QWRs are used as resonators. In yet other embodiments other resonators than QWRs may be used, for example Helmholtz resonators.

Helmholtz Resonators with Joint Compliance Cavity

Due to the small structures and the limited space available in an earpad, ensuring a relatively low resonance frequency $f_R$ (for example below 1 kHz) may be difficult. Therefore, in the embodiment described here, Helmholtz resonators (HR) are used as the resonators in an earpad in order to attenuate an impinging external sound source and exploit the locally coherent nature of the sound wave in the leak channel. In this embodiment, compliance cavities of a group of HRs are combined into a larger joint compliance cavity.

In general, a HR may comprise a mass channel (for example a bottle neck) and compliance cavity (for example the body of a bottle). The mass channel is connected to the compliance cavity, wherein the mass channel may be much smaller in volume compared to the compliance cavity.

Figure 8:
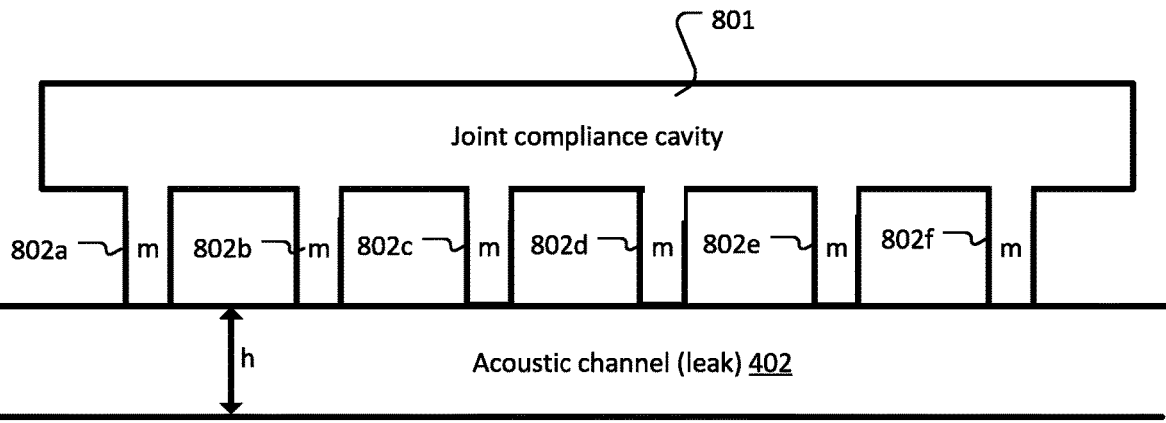
FIG. 8 shows Helmholtz resonators comprising a joint compliance cavity.

FIG. 8 shows Helmholtz resonators (HR) embedded within an earpad, the Helmholtz resonators comprising a joint compliance cavity. Each HR comprises a mass channel 802a, ..., 802f and all the HRs comprise a joint compliance cavity 801. The mass channels 802a, ..., 802f of the HRs are directly coupled to an acoustic leak channel 402, which has a height h.

Figure 9:
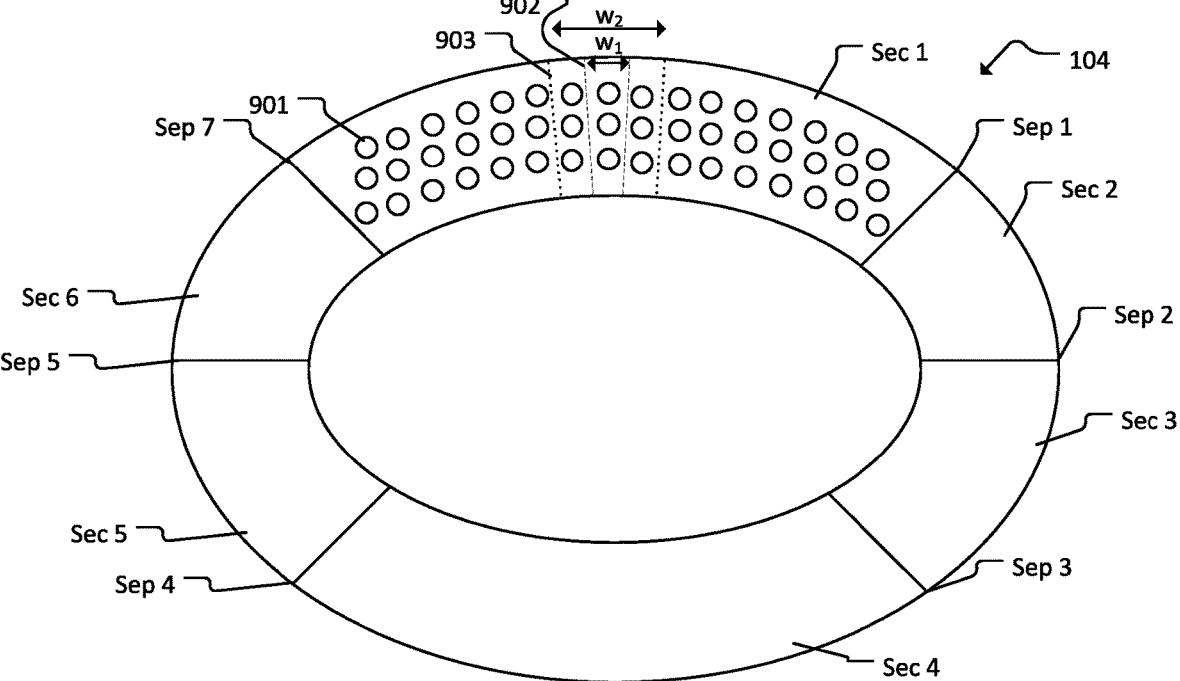
FIG. 9 shows an earpad comprising Helmholtz resonators with a plurality of joined compliance cavities.

FIG. 9 shows an earpad comprising Helmholtz resonators with a plurality of joined compliance cavities. The earpad 104 is divided into a plurality of sections Sec1, ..., Sec7. The different sections Sec1, ..., Sec7 (that is the layer of the joint compliance cavity as well as the layer of the mass channels) are separated from each other by separations Sep1, ..., Sep7. These separations Sep1, ..., Sep7 may be made of another material than the mass channels for example plastic.

Each of the sections Sec1, ..., Sec7 comprises one joint compliance cavity and one or more mass channels 901 sharing the respective joint compliance cavity. Each mass channel 901 together with the joint compliance cavity forms a respective HR. The mass channels 901 may be spaced regularly and equidistant to each other in each section.

The resonance frequency $f_R$ of the HRs, the impedance $Z_R$ of the HRs and the density $\Phi_R$ of the HRs may be chosen different or similar in each of the different sections Sec1, ..., Sec7.

A first acoustic leak channel 902 may have the size $w_1$, wherein the area of the leak channel 901 includes 3 mass channels in section Sec1 of the earpad 104. Because a relatively small number of mass channels (compared to all the mass channels within a section), sharing one significantly larger compliance cavity section in Sec1, their reso-
nance frequency may be very low.

Still further, a second acoustic leak channel 903 may have
the size $w_2$, which means that more mass channels (in this
example 9) couple to the second acoustic leak channel 903
and become activated to work on the same joint compliance
cavity of section Sec1. As a result, the effective compliance
cavity for each mass channel is reduced and the resonance
frequency of the HRs may increase. Thereby, a higher
degree of control over the range of resonance frequencies is
retained and can be applied for a range of cases.

As described above the periodicity of the resonators/mass
channels of the resonators (i.e. the meta atoms) may be
important. Naturally, a perfect periodicity may not always be
possible to maintain. However, as long as the resonators/
mass channels of the resonators are significantly smaller
than the wavelength, relatively small deviations from peri-
odicity may be no problem.

For example, the HRs with a joint compliance cavity may
be designed as follows: A block made of silicone which has
a width of 2 cm (x-axis), a height of 2 cm (y-axis) and a
depth 4 cm (z-axis) may be used. In a in an equidistant grid
structure 32 holes with a diameter of 1 mm are drilled into
the silicone block along the z-axis, wherein each drilled hole
is 0.5 cm deep. Each hole constitutes a mass channel of an
HR. The combined cavity (for example in section Sec1) may
have a face coupling to the mass channels of area of 2 cm×4
cm and a height of 1.5 cm. It may be assumed that the
channel leak may have a height of h=1 mm, and a width of
w=5 mm.

The earpad 104 with the resonators may be housed in a
housing (for example the hard-shell housing 103 see also
FIG. 1). There are no further restrictions on the housing to
work together with the earpad 104 comprising the resonators
as described above. For example, the housing may be made
of an acoustically rigid material (e.g. mechanically rigid
material like plastic or metal, or the like) or use a highly
absorbing foam.

In the embodiments described with above, the general
principles of the embodiments are described using the
example of a circumaural headphone. It should however be
noted that the principles can also be applied to on-ear
headphones. Leakage of external sound may also happen
when an earpad of an on-ear headphone rests on the ear. The
principles of the embodiments allow to attenuate sound
leakage also in such scenarios. In yet another embodiment
the principles may be applied to (circumaural) hearing
protections. Earpads of hearing protections configured
according to the teachings above may also allow to protect
against external sound sources.

In other embodiments a headphone may comprise an
active noise cancellation system which is foreseen to per-
form noise reduction on the external sound source. However,
current noise cancellation systems may only be able to
perform noise cancellation to attenuate sound coming from
an external noise source for frequencies up to 1.5 kHz. This
leaves a wide range of potential external sound sources
which may not be attenuated by active noise cancellation
systems. Accordingly, applying an earpad according to the
embodiments described above to headphones with active
noise cancellation system may also improve sound insula-
tion.

Note that the present technology can also be configured as
described below:

(1) An earpad (104) comprising one or more acoustic
resonators (401) coupled to a contact face (104*a*) of the
earpad (104) that is configured to interface with a user's head (105), the acoustic resonators (401) being config-
ured to attenuate leakage of parasitic sound (106).

(2) The earpad (104) of (1), wherein the resonators (401)
are Helmholtz resonators, or Quarter Wavelength Reso-
nators, or membrane resonators or active acoustic reso-
nators.

(3) The earpad (104) of (1) or (2), wherein the acoustic
resonators (401) are configured to attenuate the propa-
gation of parasitic sound (106) based on a specific
acoustic impedance ($Z_R$) of the resonators (401) and a
surface porosity ($\Phi_R$) due to the resonators (401).

(4) The earpad (104) of anyone of (1) to (3), wherein
interfaces to the acoustic resonators (401) are located at
the contact face (104*a*) of the earpad (104).

(5) The earpad (104) of anyone of (1) to (4), wherein the
earpad comprises a core material and a cover material,
the cover material acting as the contact face (104*a*) of
the earpad (104), wherein the cover material is perfo-
rated at the areas of the interfaces of the resonators
(401).

(6) The earpad (104) of anyone of (1) to (5), wherein the
acoustic resonators (401) are configured to attenuate
the propagation of parasitic sound (106) within a pre-
defined target frequency band (F).

(7) The earpad (104) of (6), wherein the predefined target
frequency band (F) is defined by the impedance ($Z_R$) of
the resonators (401) the surface porosity ($\Phi_R$) due to
the resonators (401) and a resonance frequency ($f_R$) of
the resonators (401).

(8) The earpad (104) of (7), wherein the lower limit ($f_{low}$)
of the frequency band (F) is based on the resonance
frequency ($f_R$) of the resonators (401).

(9) The earpad (104) of anyone of (3) to (8), wherein the
surface porosity due to the resonators ($\Phi_R$) is 0.4.

(10) The earpad (104) of anyone of (3) to (9), wherein the
specific acoustic impedance ($Z_R$) of the resonators ($Z_R$)
is frequency dependent.

(11) The earpad (104) of anyone of (1) to (10), wherein
the resonators (401) are Helmholtz resonators, each
Helmholtz resonator comprising a mass channel and a
compliance cavity.

(12) The earpad (104) of (11), wherein the compliance
cavities of the Helmholtz Resonators are combined into
a joint compliance cavity (801) connected to each of
the mass channels (802*a*; . . . ; 802*f*) of the Helmholtz
Resonators.

(13) The earpad (104) of (12), wherein the earpad com-
prises a plurality sections (Sec1, . . . , Sec7), each of the
sections (Sec1; . . . ; Sec7) comprising one joint
compliance cavity (801) and a plurality of mass chan-
nels (802*a*; . . . ; 802*f*) connected to the one joint
compliance cavity (801).

(14) The earpad (104) of (13), wherein the plurality of
sections (Sec1, . . . , Sec7) are separated from each
other.

(15) An on-ear headphone or a circumaural headphone
(100) which comprises the earpad (104) of anyone of
(1) to (14).

(16) A circumaural hearing protection which comprises
the earpad (104) of anyone of (1) to (14).

The invention claimed is:

1. An earpad, comprising:
one or more acoustic resonators coupled to a contact face
of the earpad that is configured to interface with a
user's head, the one or more acoustic resonators being
configured to attenuate leakage of parasitic sound,
wherein the one or more acoustic resonators are configured to attenuate propagation of parasitic sound based on at least one of a specific acoustic impedance ($Z_R$) of the one or more resonators and a surface porosity ($\Phi_R$) due to the one or more resonators, and wherein interfaces to the one or more acoustic resonators are located at the contact face of the earpad.

2. The earpad of claim 1, wherein:

the one or more resonators are one or more Helmholtz resonators, one or more Quarter Wavelength Resonators, one or more membrane resonators, or one or more active acoustic resonators.

3. The earpad of claim 1, wherein:

the one or more acoustic resonators are configured to attenuate the propagation of parasitic sound based on the specific acoustic impedance ($Z_R$) of the one or more resonators and the surface porosity ($\Phi_R$) due to the one or more resonators.

4. The earpad of claim 1, wherein:

the one or more acoustic resonators are configured to attenuate the propagation of parasitic sound within a predefined target frequency band (F).

5. The earpad of claim 4, wherein:

the predefined target frequency band (F) is defined by the impedance ($Z_R$) of the one or more resonators, the surface porosity ($\Phi_R$) due to the one or more resonators, and a resonance frequency ($f_R$) of the one or more resonators.

6. The earpad of claim 5, wherein:

a lower limit ($f_{low}$) of the frequency band (F) is based on the resonance frequency ($f_R$) of the one or more resonators.

7. The earpad of claim 3, wherein:

the surface porosity due to the one or more resonators ($\Phi_R$) is 0.4.

8. The earpad of claim 3, wherein:

the specific acoustic impedance ($Z_R$) of the one or more resonators is frequency dependent.

9. The earpad of claim 1, wherein:

the one or more resonators are one or more Helmholtz resonators, each Helmholtz resonator among the one or more Helmholtz resonators comprising a mass channel and a compliance cavity.

10. The earpad of claim 9, wherein:

the compliance cavities of the one or more Helmholtz Resonators are combined into a joint compliance cavity connected to each of the mass channels of the one or more Helmholtz Resonators.

11. The earpad of claim 10, wherein:

the earpad comprises a plurality of sections, each of the sections comprising one joint compliance cavity and a plurality of mass channels connected to the one joint compliance cavity.

12. The earpad of claim 11, wherein:

the plurality of sections are separated from each other.

13. The earpad of claim 1, wherein;

the contact face of the earpad comprises the one or more acoustic resonators, and a contact face of the one or more acoustic resonators is a periodic plane having a lattice including a lattice constant, and the lattice constant in at least two directions is the same.

14. The earpad of claim 1, wherein:

the one or more acoustic resonators and a parasitic leak channel together form an absorbing acoustic meta material (AMM).

15. An on-ear headphone or a circumaural headphone, comprising:

the earpad of claim 1.

16. A circumaural hearing protection, comprising:

the earpad of claim 1.

17. An earpad, comprising:

one or more acoustic resonators coupled to a contact face of the earpad that is configured to interface with a user's head, the one or more acoustic resonators being configured to attenuate leakage of parasitic sound, wherein the one or more acoustic resonators are configured to attenuate propagation of parasitic sound within a predefined target frequency band (F), the predefined target frequency band (F) is defined by impedance ($Z_R$) of the one or more resonators, a surface porosity ($\Phi_R$) due to the one or more resonators, and a resonance frequency ($f_R$) of the one or more resonators, and the earpad comprises a core material and a cover material, the cover material acting as the contact face of the earpad, wherein the cover material is perforated at areas of interfaces of the one or more resonators.

18. The earpad of claim 17, wherein:

the one or more acoustic resonators and a parasitic leak channel together form an absorbing acoustic meta material (AMM).

19. An earpad, comprising:

one or more acoustic resonators coupled to a contact face of the earpad that is configured to interface with a user's head, the one or more acoustic resonators being configured to attenuate leakage of parasitic sound, wherein the one or more resonators are one or more Helmholtz resonators, each Helmholtz resonator among the one or more Helmholtz resonators comprising a mass channel and a compliance cavity, the compliance cavities of the one or more Helmholtz Resonators are combined into a joint compliance cavity connected to each of the mass channels of the one or more Helmholtz Resonators, and the earpad comprises a plurality sections, each of the sections comprising one joint compliance cavity and a plurality of mass channels connected to the one joint compliance cavity.

20. The earpad of claim 19, wherein:

the one or more acoustic resonators and a parasitic leak channel together form an absorbing acoustic meta material (AMM).

\* \* \* \* \*